(12) United States Patent
Yun et al.

(10) Patent No.: US 9,194,806 B2
(45) Date of Patent: Nov. 24, 2015

(54) MEANS FOR DETECTING OXYGEN FREE RADICALS IN HUMAN BODY

(71) Applicant: DFI Co.,Ltd., Gimhae-si, Gyeongsangnam-do (KR)

(72) Inventors: Jung-geon Yun, Gimhae-si (KR); Yong-ae Park, Busan (KR); Tae-wan Kim, Busan (KR); Sang-hoon Kang, Busan (KR)

(73) Assignee: DFI CO., LTD., Gimhae-shi (KR)

( * ) Notice: Subject to any disclaimer, the term of this patent is extended or adjusted under 35 U.S.C. 154(b) by 0 days.

(21) Appl. No.: 14/258,192

(22) Filed: Apr. 22, 2014

(65) Prior Publication Data

US 2014/0302613 A1    Oct. 9, 2014

Related U.S. Application Data

(63) Continuation of application No. PCT/KR2012/007110, filed on Sep. 5, 2012.

(30) Foreign Application Priority Data

Jan. 31, 2012   (KR) .......................... 10-2012-0009981

(51) Int. Cl.
*G01N 21/63* (2006.01)
*G01N 21/62* (2006.01)
*G01N 21/00* (2006.01)
*G01N 31/22* (2006.01)
*G01N 31/00* (2006.01)
*G01N 21/78* (2006.01)
*G01N 33/52* (2006.01)

(52) U.S. Cl.
CPC .............. *G01N 21/78* (2013.01); *G01N 33/523* (2013.01); *Y10T 436/20* (2015.01)

(58) Field of Classification Search
CPC ............ G01N 21/6408; G01N 31/225; G01N 21/636; G01N 21/63; G01N 21/62; G01N 21/00; G01N 31/223; G01N 31/22; G01N 31/00; A61B 5/097; A61B 5/08; A61B 5/00
USPC ........................................................ 436/127
See application file for complete search history.

(56) References Cited

U.S. PATENT DOCUMENTS

| | | | | |
|---|---|---|---|---|
| 6,165,797 | A  * | 12/2000 | Halstead | 436/128 |
| 6,689,617 | B1 * | 2/2004 | Abels | 436/128 |
| 2002/0072125 | A1 * | 6/2002 | Morelle et al. | 436/128 |
| 2005/0123439 | A1 * | 6/2005 | Patton et al. | 422/56 |
| 2006/0073604 | A1 * | 4/2006 | Yoon et al. | 436/128 |
| 2007/0287183 | A1 * | 12/2007 | Wagner et al. | 436/20 |

* cited by examiner

*Primary Examiner* — Christine T Mui
(74) *Attorney, Agent, or Firm* — Park & Associates IP Law, P.C.

(57) ABSTRACT

A means for detecting active oxygen in the human body, which quantitatively detects the amount of active oxygen remaining in the body by applying urine to a detection paper, and is characterized by providing a means for detecting active oxygen in the human body, which detects the amount of active oxygen by submerging a test strip into urine, on which has been applied a color indicating agent that changes color by reacting with malondialdehyde (MDA) and to which has been coupled a support stick, and observing color change. The present invention can affordably and simply identify active oxygen, because the test strip changes color when simply wetted with urine and the test does not require additional technically skilled laboratory staff or expensive equipment. Also, the invention enables simple testing regardless of time and space since a specific facility is unnecessary for the test, thereby providing another advantage of general usage.

8 Claims, 1 Drawing Sheet

[formation of red dye, TBA2-MDA]

MEANS FOR DETECTING OXYGEN FREE RADICALS IN HUMAN BODY

REFERENCE TO RELATED APPLICATIONS

This is a continuation of pending International Patent Application PCT/KR2012/007110 filed on Sep. 5, 2012, which designates the United States and claims priority of Korean Patent Application No. 10-2012-0009981 filed on Jan. 31, 2012, the entire contents of which are incorporated herein by reference.

FIELD OF THE INVENTION

The present invention relates to a means for detecting oxygen-free radicals which are harmful in the human body, and more specifically, the present invention relates to a means for quantitatively detecting the amount of oxygen-free radicals present in the human body with improved convenience and promptness by dipping a test strip into a subject's urine.

BACKGROUND OF THE INVENTION

Maintaining an (ATP) energy supply in humans sufficient for survival and activity requires the metabolism of carbohydrates and lipids. Humans cannot survive without oxygen being supplied into the cells. During oxygen metabolism in the body, however, free radicals, also called hazardous or active oxygen, are generated as a byproduct. The active oxygen harms the body in various ways, for example, they form lipid peroxides in the tissues of human body. In other words, the increase in active oxygen increases lipid peroxides, and excessive lipid peroxides can cause various diseases such as stroke, cardiac infarction, myocardial infarction, alcoholic hepatitis, etc., due to cerebrovascular disorders.

Accordingly, it is very important to quantitatively check the amount of active oxygen as an index for health prevention, but the harmful active oxygen is highly reactive and thus it is difficult to directly measure their level. As such, the amount of lipid peroxides caused by active oxygen is indirectly detected and often used as a marker. In general, malondialdehyde (MDA) is a marker serving as one of the methods used to estimate the level of lipid peroxidation. It can be easily detected in blood tissues and used as a marker for health evaluation. By measuring MDA, the level of lipid peroxidation can be elucidated. The level of MDA is often detected using blood or urine. MDA detection can be done using an HLPC or thiobarbituric acid reactant substrate (TBARS) method, and more frequently via TBARS method because HPLC requires expensive equipment. However, the TBARS method also has the disadvantages that the method also requires boiling of a sample, and necessitates a sophisticated process of extraction using an organic solvent, thus requiring a relatively long time for the process and also requires additional technically trained laboratory staff to perform the process. Additionally, the method has an additional problem that it allows materials other than MDA to react, thus deteriorating its specificity.

SUMMARY OF THE INVENTION

In order to solve the above-described problem of the existing art, the present invention is directed to providing a means for detecting active oxygen in the human body, which enables a quantitative detection of malondialdehyde (MDA) based on color change by simply wetting a detection paper in a subject's urine, thus not requiring additional skilled lab staff or additional expensive equipment.

The present invention is not limited hereto, and other objectives not described above will be more clearly understood from what has been set forth hereunder.

In an exemplary embodiment, the present invention provides a means for detecting active oxygen in the human body, which by detects the amount of active oxygen by submerging a test strip into urine, on which has been applied a color indicating agent that changes color by reacting with MDA and to which has been coupled a support stick, and observing color change.

Preferably, the test strip may use 1,3-dimethyl-2-thiobarbituric acid (TBA) as a color indicating agent. The test strip may be prepared by submerging it in a first solution prepared by mixing 10-30% of citric acid, and 20-30% of trisodium citrate using distilled water as a solvent followed by drying at about 50 to 60° C. for about 20 to 30 minutes; and then submerging it in a second solution prepared by mixing 2-3% of TBA as a color indicating agent, and 2-5% of polyvinylpyrrolidone (PVP) using ethyl alcohol as a solvent, respectively.

Additionally, the test strip may use basic fuchsine as a color indicating agent, and prepared by submerging it in a first solution prepared by submerging it in a first solution prepared by mixing 20-30% of Na-Metabisulfite, and 20-30% of NDS Acid using distilled water as a solvent; and then submerging it in a second solution prepared by mixing 10-30% of basic fuchsine as a color indicating agent using ethyl alcohol as a solvent followed by drying; or the test strip may use pararosaniline hydrochloride as a color indicating agent, and prepared by submerging it in a first solution prepared by mixing 20-40% of sulfosalicylic acid, 20-40% of NDS acid, and 5-15% of urea using distilled water as a solvent; and then submerging it in a second solution prepared by mixing 5-15% of pararosaniline hydrochloride, 20-40% of sulfosalicylic acid, and 20-40% of NDS acid using distilled water as a solvent, respectively.

Additionally, the test strip may be prepared using glycine as a color indicating agent by submerging it in a solution prepared by mixing 10-30% of glycine and 20-40% of sodium sulfate using distilled water as a solvent, followed by drying.

The present invention has advantages that it can easily and cost-effectively detect active oxygen based on color change by simply wetting a test strip thus not necessitating additional professionals or expensive equipment.

In addition, the test of the present invention does not require any particular facility but can be easily conducted without any specific limitations on place and time thus being applicable to a general use.

BRIEF DESCRIPTION OF THE DRAWINGS

FIG. 3 is a picture showing the color change according to the amount of active oxygen contained in a subject's urine in

DETAILED DESCRIPTION OF THE INVENTION

Hereinafter reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims. Unless specifically stated or obvious from context, as used herein, the term "about" is understood as within a range of normal tolerance in the art with regard to a unique manufacture of a product or a material, and also to prevent the unjustifiable use of the contents of the accurate and exact values disclosed hereinbelow by an unscrupulous infringer.

The gist of the present invention lies in identifying the amount of active oxygen present in human body by submerging a test means, provided with a color indicator that quantitatively reacts with MDA, a marker for lipid peroxide present in urine formed by active oxygen in the body, into a subject's urine based on color change indicated on the test means.

Figure 1:
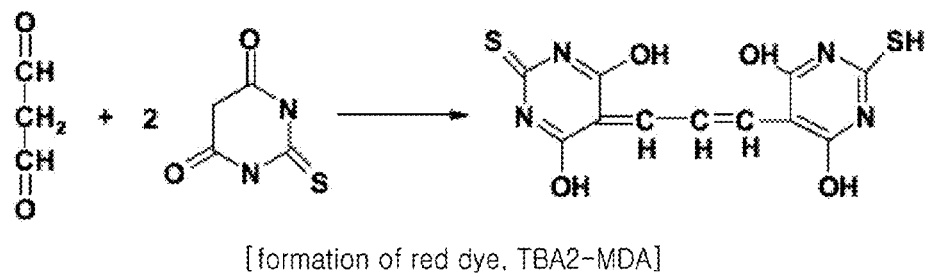
FIG. 1 is a reaction scheme showing the formation of a red dye by the reaction between malondialdehyde and TBA as markers.

More specifically, as shown in FIG. 1, two 1,3-diethyl-2-thiobarbituric acid (hereinafter referred to as TBA) molecules react with one MDA molecule to form a red dye, TBA2-MDA. Accordingly, the amount of color change of the red dye occurs according to the level of the reaction, and the level of the color change may be quantitatively analyzed using an absorptiometer or detected by comparing using a color reference chart.

Accordingly, by submerging a test strip containing TBA reagent, a reaction reagent as mentioned above, into urine, the amount of active oxygen present in the body may be easily detected based on the simple color change due to its quantitative reaction with MDA, thereby enabling a simple and convenient measurement of active oxygen in the body. In this regard, the inventors of the present invention have made numerous efforts to provide the color indicating agent in the form of a test strip, and as a result, succeeded in preparing one as such. The details of the present invention will be described in further detail herein below.

Preparation of Test Strips

In general, a test strip for urine testing or diagnosis may be prepared by dissolving a buffer solution, a polymer/surfactant, and an indicator for materials to be tested at a particular concentration in solvents, and submerging a paper strip therein. This is to maintain an optimum condition for the indicator to react with a reactant, and also to prevent the indicator contained in the test strip and other reagents from being eluted into a sample. In the present invention, basic fuchsine, pararosaniline hydrochloride, glycine and TBA, which are color indicating agents currently known to react with MDA to produce a color, were used to prepare various buffer solution compositions, polymers/surfactants solutions, etc., thereby preparing suitable test strips.

EXAMPLE 1

Herein below are explanations when TBA is used as a color indicating agent.

1) Buffer Solutions

Determining an appropriate pH condition for an indicator to react, and types and concentrations of buffers not only enables the provision an optimum condition for the indicator to react but also prevents the indicator from being affected by the pH of a sample when the test strip is submerged into a sample having a totally different pH from that of the indicator constituted therein. This was intended that only the shift of pKa value of the indicator, instead of pH change, can have an influence on the color change of the test strip. The color development of a selected indicator was shown to be appropriate to distinguish negative and positive results at pH 2-4, and there was deterioration in color development when the pH was below 2 or above 4.

Experiments were performed using an anionic buffer, which lowers the pH of a given solution by releasing electrons in the solution, at arbitrary concentrations selected from the group consisting of citric acid, malonic acid, sulfosalicylic acid, 1,5-Naphthalenedisulfonic acid tetrahydrate (NDS acid), tartaric acid, citraconic acid, cyanoacetic acid, sarcosin, etc. The experiments revealed that color development was easily confirmed in the range of 10-30 parts by weight of citric acid relative to 100 parts by weight of a basic solvent. In addition, citric acid as an anionic buffer lowers the pH of a given solution by releasing the retaining electrons upon the presence of metal cations. Accordingly, experiments were performed using a combination of cationic buffer reagents such as potassium citrate, borax, potassium phosphate, trisodium citrate, etc., and the diagnosis of color development was made possible at a stable level, and the color development was most discernible when pH was controlled in the range of 10-30 parts by weight of trisodium citrate.

2) Surfactants

Surfactants are dispersion reagents which enable the maintenance of the constituents of a test strip in a dried state, serve as a stabilizer and maintain uniform color change. The surfactants used in the present invention are polymers that intensify colors, and serve to stabilize color formation of an indicator and increase its reactivity, thereby exhibiting high accuracy of the color development. A polymer having a molecular weight of about 400 to about 25,000, which is known to increase color formation and dose response of indicators and deteriorate the basic color in a negative result was added in the experiments, and the change in color was confirmed by submerging a test strip containing the additive in both negative and positive test solutions, and the type of surfactants and their concentration were determined therefrom. From experiments which were performed using reagents such as SDS, TritonX-100, dodecybenzene sulfonic acid (LBS), doctyl sulfosuccinate, and glycerol as a surfactant, it was confirmed that TritonX-100 showed deterioration in color development and LBS showed a later increase in color development, but no significant changes were observed with other reagents. As a result, the amount of the surfactants suitable for each color indicating agent was determined to be in the range of 0.1-2 parts by weight.

3) Color Indicating Agents

It was confirmed that color development was increased proportional to the amount of TBA. However, due to its solubility issue on alcoholic solvents, the optimum concentration was determined to be in the range of 2-3 parts by weight, and when the concentration exceeded 3 parts by weight there was no significant increase in color development.

4) Polymers

Dispersion particles as components of TBA, a color indicating agent, in fact consist of bead-like particles. Their mass density can be sufficiently regulated in an electrolytic solvent, and the rate of particle precipitation depends not only on the diameter of the particles but also on the density difference between the particles and its transport solution. In particular, a stable solution can be stabilized by harmonizing the density of the electrolytic solvent along with the polymers used in the beads. Furthermore, polymers are preferred to be water-soluble in order to saturate the density of the electrolytic solvent. In addition, the test strip containing the stabilizer reagent helps to maintain color development and a negative color during the effective period if it is stored in a bottle after its manufacture.

Hydroxy cyclo dextrin, polymethylmaleic acid, and anhydrous polyvinylmaleic acid-119 were tested as a stabilizer, but test strips containing the above compounds were shown to prevent color development and were thus difficult to apply to recognizing the concentration.

Polyvinylpyrrolidine (PVP) (10, 40 and 55) was determined to be useful because it did not have any significant influence on the molecular weight, and its optimum amount was determined to be in the range of 2-5 parts by weight.

5) Preparation of Test Strips

Based on the above experiments, a first solution constituting a butter solution and a second solution constituting a color indicating agent are prepared using Whatman papers, respectively.

Firstly, the first solution is prepared by mixing 10-30 parts by weight of citric acid, and 20-30 parts by weight of trisodium citrate using 100 parts by weight of distilled water as a solvent. Then, the second solution is prepared by mixing 2-3 parts by weight of TBA as a color indicating agent, 0.1-2 parts by weight of Triton X-100, and 2-5 parts by weight of PVP using 100 parts by weight of ethyl alcohol as a solvent.

Upon completion of preparing the first and second solutions as described above, test strips such as Whatman paper, which are absorbent to solutions as those prepared above, are submerged therein thereby allowing TBA to be sufficiently absorbed thereinto. More specifically, the test strips, after being submerged into the first solution, are dried in a device such as a drying oven set at 50 to about 60° C. for about 20 to about 30 minutes to allow the first solution to be absorbed into the test strips, and then submerged again into the second solution, followed by drying in a drying oven, thereby obtaining a final test strip. Finally, the thus prepared test strips were shown to develop a red color by reacting with MDA, are very stable at room temperature, and were able to measure up to 0.5 mmol/L as the lowest sensitivity level.

6) Preparation of a Detection Means

After the TBA test strips are prepared as described above, they are cut into a suitable size and coupled to support sticks prepared in a rectangular form, thereby manufacturing a detection means. In particular, the support sticks should be carefully made of a material which is neither reactive to the TBA test strips nor to any of urine components, wherein the TBA test strips are coupled on their front part. To this end, the support sticks may be preferably made using a conventional polymer such as polystyrene or polyacryl, in various forms including a film type and a rod. The TBA test strips are coupled on the front part of the support sticks, and the coupling of the test strips may be performed using a dual adhesive tape or an adhesive.

Furthermore, the thus prepared detection means is preferably stored in a place with a dehumidifying agent such as silica gel and used when necessary because it is sensitive to humidity.

EXAMPLE 2

Use of basic fuchsine and pararosaniline hydrochloride as a color indicating agent are briefly explained herein below.

1) Buffer Solutions

As a result of conducting experiments using various anionic and cationic buffers as in Example 1, optimum pH conditions, and types and concentrations of buffers suitable for indicators were determined thereby obtaining the optimum condition for indicators.

2) Color Indicating Agents

It was confirmed that the color development was increased proportional to the amount of an indicator. However, the amount of each indicator to be used according to its physical properties, and selection of a solvent thereof were established via various experiments.

3) Preparation of Test Strips

Based on the above experiments, a first solution constituting the buffer solution and a second solution constituting the color indicating agent are prepared, respectively.

First, the use of basic fuchsine as a color indicating agent is explained herein below. The first solution is prepared by mixing 20-30 parts by weight of Na-Metabisulfite, and 20-30 parts by weight of NDS Acid using 100 parts by weight of distilled water as a solvent. And the second solution is prepared by mixing 10-30 parts by weight of basic fuchsine as a color indicating agent using 100 parts by weight of ethyl alcohol.

Upon completion of preparing the first and second solutions as described above, Whatman papers were submerged in the first solution in the same manner as in the Example and dried, and then the resultant was submerged in the second solution and then dried thereby obtaining final test strips. Here, the final test strips developed red colors but the colors were a bit deteriorated as compared to those in Example 1).

The use of pararosaniline hydrochloride as a color indicating agent is explained herein below. The first solution is prepared by mixing 20-40 parts by weight of sulfosalicylic acid, 20-40 parts by weight of NDS acid, and 5-15 parts by weight of urea using 100 parts by weight of distilled water as a solvent.

And the second solution is prepared by mixing 5-15 parts by weight of pararosaniline hydrochloride, 20-40 parts by weight of sulfosalicylic acid, and 20-40 parts by weight of NDS acid using 100 parts by weight of distilled water as a solvent. The test strips are prepared in the same manner, and they developed red colors. The stability was poor at room temperature, but increased to an allowable level when the test strips were stored in a refrigerator.

EXAMPLE 3

The use of glycine as a color indicating agent is briefly explained herein below.

When glycine is used, the solution may be prepared by mixing 10-30 parts by weight of glycine and 20-40 parts by weight of sodium sulfate using 100 parts by weight of distilled water as a solvent, not requiring the preparation of additional buffer solutions as in Example 1) and Example 2).

In this case, the final test strips are prepared by submerging Whatman paper into the mixed solution followed by drying, and they developed yellow colors by reacting with MDA. They had effective stability at room temperature but sensitivity of color development at low concentrations was a bit deteriorated.

Test Example 1

Samples containing MDA at an appropriate concentration are prepared. The samples are prepared to have appropriate concentrations of 0.2 0.5 1, 2.5, 5, 7.5 and 10 mmol/L. The suitability of the samples regarding their MDA concentration was tested via ELISA assay.

Results

Figure 2A:
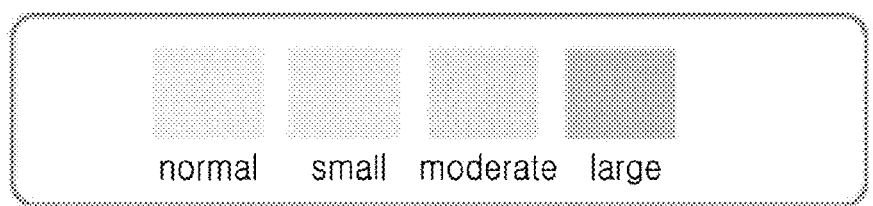
FIG. 2A is a picture of a color reference chart.
Figure 2B:
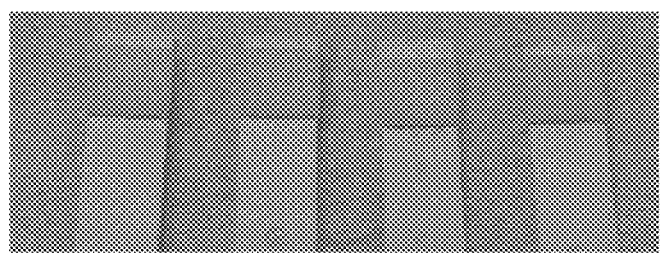
FIG. 2B is a picture showing color changes in response to the amount of MDA, and color contrast against the color reference chart, as measured by a standard solution in a means for detecting active oxygen according to an exemplary embodiment of the present invention.

When the thus prepared samples were dipped into the detection means TBA, components contained in the test strips of the detection means reacted with MDA components in the sample solution thereby incurring a color change, and it was confirmed that the higher the concentration of MDA the darker the color development. Referring to the pictures, FIG. 2A represents dipsticks, and FIG. 2B shows an image where a color indicating agent reacted with MDA and caused a color change. As shown in the figures, the amount of MDA detected can be easily identified by comparing the color change and the color reference chart, and thus can be visually confirmed rather easily. The color change may be measured in terms of quantitative concentration based on color change using an absorptiometer, and a user can simply confirm it based on the recognition of visual color change according to the color reference chart, wherein the results were divided into four different categories being considered as normal at a concentration of 0-0.3 mmol/L; small at a concentration of 0.4 or higher; moderate at a concentration between 2.5 and 6 mmol/L; and large at a concentration of 6 mmol/L or higher. Additionally, referring to Table 1 below where the means of the present invention was compared with that of ELISA, it was confirmed that the means of the present invention quantitatively reacted with MDA.

TABLE 1

| Conc. (mmol/L) | Detection means of the present invention | ELISA | Remarks |
|---|---|---|---|
| 0 | Normal | 0.00 | |
| 0.2 | Normal | 0.22 | |
| 0.5 | Small | 0.47 | |
| 1 | Small | 1.12 | |
| 2.5 | Moderate | 2.67 | |
| 5 | Moderate | 5.14 | |
| 7.5 | Large | 7.41 | |
| 10 | Large | 9.87 | |

Test Example 2

In an embodiment of the present invention, five males and five females in their 20s were selected in order to validate whether the means of the present invention is effective to measure the amount of active oxygen present in the human body, and their urine samples were collected and analyzed. For comparison purposes, the results were compared with that of ELISA assay commonly used in the related art.

TABLE 2

| Subject | Detection means of the present invention | ELISA (mmol/L) | Remarks |
|---|---|---|---|
| 1 | Normal | 0.19 | |
| 2 | Normal | 0.3 | |
| 3 | Large | 8.89 | |
| 4 | Moderate | 4.5 | |
| 5 | Normal | 0.28 | |
| 6 | Small | 1.2 | |
| 7 | Large | 8.1 | |
| 8 | Small | 0.76 | |
| 9 | Small | 0.82 | |
| 10 | Moderate | 4.59 | |

Figure 3:
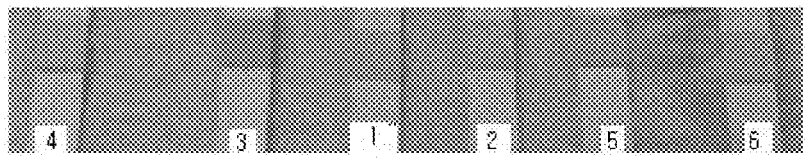

As shown in Table 2 above, the amount of active oxygen detected in urine was very similar to those obtained via ELISA assay using expensive equipment. In other words, as shown in the picture of FIG. 3, various color changes were shown in the detection means dipped into urine. In particular, the color changes shown in subject no. 1 to subject no. 6 were apparently distinguishable based on the color reference chart, where the color change is due to the amount of active oxygen contained in the urine. In light of the similar results between those based on the color change and those via ELISA assay, it was confirmed that the quantitative measurement of active oxygen is possible via simple observation after simply wetting the detection means in a subject's urine.

The present invention relates to a means for detecting active oxygen which is harmful to the human body. More specifically, the means of the present invention enables to quantitatively detect the amount of active oxygen present in the human body by dipping a detection paper into a subject's urine, thus being conveniently and promptly applicable in fields requiring the detection of active oxygen in the bodies.

What is claimed is:

1. A testing article for detecting active oxygen in the human body, comprising:
   a test strip coupled to a support stick, the test strip being applied with a first solution and a second solution, wherein the first solution comprises citric acid and trisodium citrate mixed in distilled water, and wherein the second solution comprises 1,3-dimethyl-2-thiobarbituric acid (TBA), Triton X-100 and polyvinylpyrrolidone (PVP) mixed in ethyl alcohol.

2. The testing article according to claim 1, wherein the first solution comprises 10-30 parts by weight of citric acid, 20-30 parts by weight of trisodium citrate and 100 parts by weight of distilled water, and wherein the second solution comprises 2-3 parts by weight of 1,3-dimethyl-2-thiobarbituric acid (TBA), 0.1-2 parts by weight of Triton X-100, 2-5 parts by weight of polyvinylpyrrolidone (PVP) and 100 parts by weight of ethyl alcohol.

3. A testing article for detecting active oxygen in the human body, comprising:
   a test strip coupled to a support stick, the test strip being applied with a first solution and a second solution, wherein the first solution comprises Na-Metabisulfite and 1,5-Naphthalenedisulfonic acid tetrahydrate (NDS) Acid mixed in distilled water, and wherein the second solution comprises basic fuchsine mixed in ethyl alcohol.

4. The testing article according to claim 3, wherein the first solution comprises 20-30 parts by weight of Na-Metabisulfite, 20-30 parts by weight of NDA Acid and 100 parts by weight of distilled water, and wherein the second solution comprises 10-30 parts by weight of the basic fuchsine and 100 parts by weight of ethyl alcohol.

5. A testing article for detecting active oxygen in the human body, comprising:
   a test strip coupled to a support stick, the test strip being applied with a first solution and a second solution, wherein the first solution comprises sulfosalicylic acid, 1,5-Naphthalenedisulfonic acid tetrahydrate (NDS) acid, and urea mixed in distilled water, and wherein the second solution comprises pararosaniline hydrochloride, sulfosalicylic acid, and NDS acid mixed in distilled water.

6. The testing article according to claim 5, wherein the first solution comprises 20-40 parts by weight of sulfosalicylic acid, 20-40 parts by weight of NDS acid, 5-15 parts by weight of urea and 100 parts by weight of distilled water, and wherein the second solution comprises 5-15 parts by weight of pararosaniline hydrochloride, 20-40 parts by weight of sulfosalicylic acid, 20-40 parts by weight of NDS acid and 100 parts by weight of distilled water.

7. A testing article for detecting active oxygen in the human body, comprising:
   a test strip coupled to a support stick, wherein the test strip is applied with a solution comprising glycine, sodium sulfate and distilled water.

8. The testing article according to claim 7, wherein the solution comprises 10-30 parts by weight of glycine and 20-40 parts by weight of sodium sulfate and 100 parts by weight of distilled water.

* * * * *